United States Patent [19]
Milani

[11] Patent Number: 5,875,488
[45] Date of Patent: Mar. 2, 1999

[54] HEADGEAR WITH PONYTAIL PULL-THROUGH

[76] Inventor: David Jerome Milani, 175A Corbett Ave., San Francisco, Calif. 94114

[21] Appl. No.: 97,857

[22] Filed: Jun. 16, 1998

[51] Int. Cl.[6] .................................................. A61F 9/00
[52] U.S. Cl. .................................. 2/12; 2/171; 2/DIG. 11
[58] Field of Search ......................... 2/12, 171, DIG. 11, 2/209.3, 209.4, 209.5, 209.7

[56] References Cited

U.S. PATENT DOCUMENTS 1,199,162  9/1916  Dickey et al. ................................ 2/12
5,598,585  2/1997  Stroup ........................................ 2/171

*Primary Examiner*—Diana L. Biefeld
*Attorney, Agent, or Firm*—Bruce H. Johnsonbaugh

[57] ABSTRACT

A visor or cap with an elastic ponytail pull-through. A pair of parallel elastic bands are utilized which exert pressure to hold the visor on the user's head. The bands are simply separated when used as a ponytail pull-through to encircle and grasp the ponytail while also simultaneously holding the visor on the user's head.

4 Claims, 2 Drawing Sheets

HEADGEAR WITH PONYTAIL PULL-THROUGH

BACKGROUND AND BRIEF SUMMARY

The present invention relates generally to headgear. More particularly, the invention pertains to a visor or cap provided with an elastic ponytail pull-through support.

The prior art includes various headgear apparel which accommodate a ponytail. For example, the Leopold U.S. Pat. No. 5,170,509 dated Dec. 15, 1992 teaches a cap with an opening formed in its back portion, allowing a ponytail to extend therethrough. A separate hairband 14 is provided to surround the user's ponytail. The primary disadvantage of Leopold is its rather cumbersome two-part design. The hair band 14 does not assist in holding the cap onto the head of the user. A separate mechanism, such as elastic band 20, must be provided to hold the cap onto the user's head. Secondly, the hairband 14 requires a separate attachment to the back of the cap, shown as 31 in FIG. 3. This results in a somewhat cumbersome mechanism for the user, in that the ponytail must be pulled through the hat opening and the hairband. Additionally, the Leopold design is relatively expensive to manufacture in that the hairband 14 is made as a separate device and is attached to the hat after the hat and hairband are manufactured. Finally, the hairband could easily become separated from the cap and lost after repeated use.

The Landis U.S. Pat. No. 5,615,414 dated Apr. 1, 1997 teaches a plastic, two-piece visor having a hair pull-through. The Landis mechanism includes two pieces, one of which could easily become lost. The specific molded plastic taught by Landis is also relatively expensive and would not "breath," allowing perspiration to build up between the user's skin and the visor.

The Armenta et al U.S. Pat. No. 5,644,799 dated Jul. 8, 1997 teaches an accessory "patch" which the user attaches to a hat. The user cuts a hole in the rear portion of the hat and stitches the patented accessory in place. The accessory has a plurality of radial slots allowing the hair to pass therethrough. This design provides no resilient material extending around the user's hair. The design would not work with a visor.

According to the present invention, a visor or cap is provided with a relatively simple ponytail pull-through made of a pair of parallel elastic bands. The elastic bands with the visor or cap of the present invention form a single, simple, yet attractive, headgear apparel. The elastic bands which form the ponytail pull-through provide two functions simultaneously. First, the elastic bands always apply a gentle tensile force keeping the headgear on the user's head. Secondly, when the elastic bands are separated and the ponytail pulled therethrough, the elastic bands encircle and grasp the ponytail and hold the ponytail in place. In contrast to the prior art, the present invention is relatively simple in design, since it is essentially a one-piece design as opposed to the Leopold two-piece design. The present invention is preferably made of absorbent fabric material, in contrast to the plastic material of the Landis visor. Furthermore, the present invention grasps the ponytail and holds the hair securely in position rather than allowing the ponytail to separate, as is the case with the Armenta et al prior art.

A primary object of the invention is to provide a cap or visor with a simple one-piece design and having a ponytail pull-through.

A further object of the invention is to provide a cap or visor having a ponytail pull-through which performs both the function of holding the cap or visor onto the user's head and also performing the function of encircling and grasping the ponytail when a ponytail is extended therethrough.

Another object of the invention is to provide a visor having a ponytail pull-through wherein those portions of the visor that contact the user's head are made of absorbent cloth.

Further objects and advantages of the invention will become apparent from the following description and the drawings wherein:

DETAILED DESCRIPTION OF THE DRAWINGS

A headgear apparel device is shown generally as 20. The embodiment shown in FIGS. 1–4 is a visor but it is understood that the invention could be applied to a cap as well.

A visor 21 is provided which shields the eyes and face of a user, as is well known in the art. Visor 21 is preferably covered with cloth fabric and sewn together to a support means, which preferably is a fabric band having a front portion 22 extending across the forehead of the user and side portions 23 and 24 extending across both sides of the user's head and across a portion of the back of the user's head, as shown best in FIG. 2. The support means or fabric band is preferably made of cotton and may include an absorbent liner to absorb perspiration and increase comfort of wearing the device.

Figure 1:
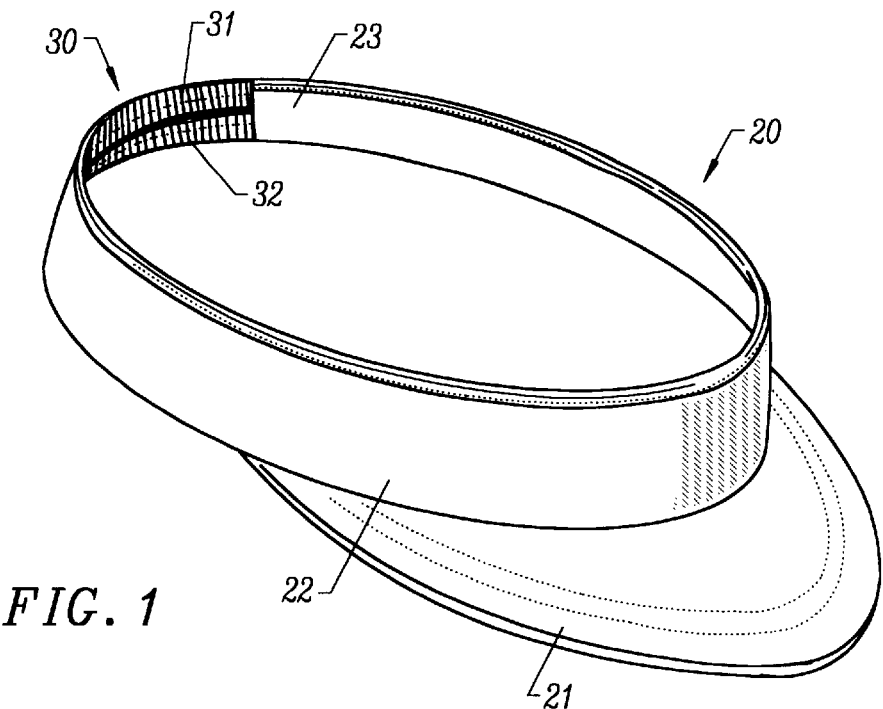
FIG. 1 is a perspective view of a visor according to the invention.
Figure 2:
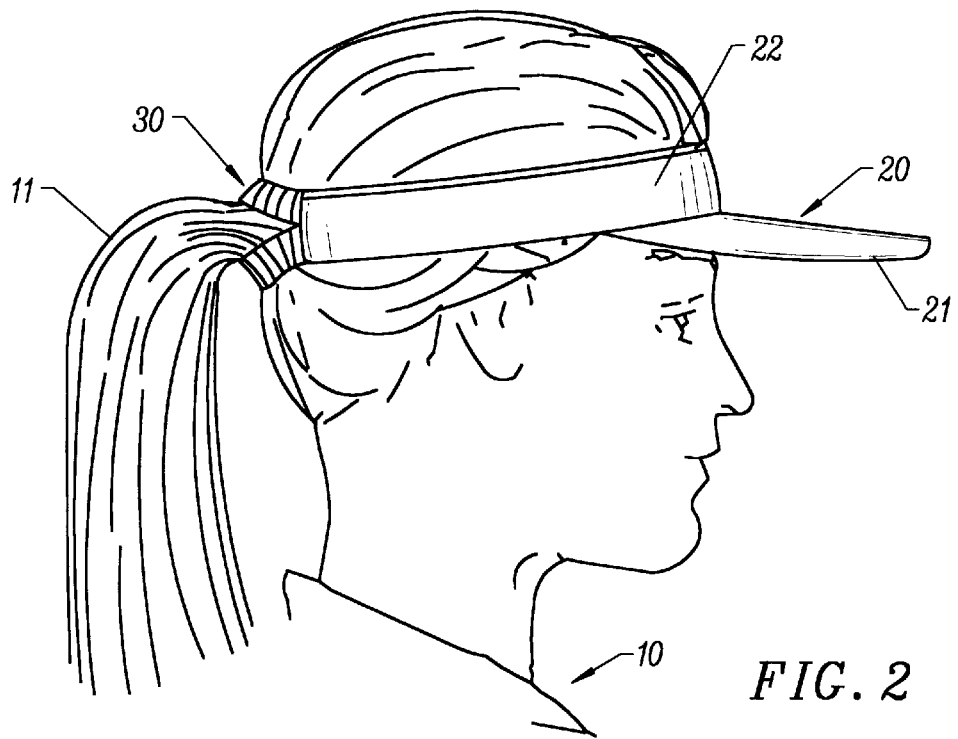
FIG. 2 shows the visor of FIG. 1 as worn by a user.
Figure 3:
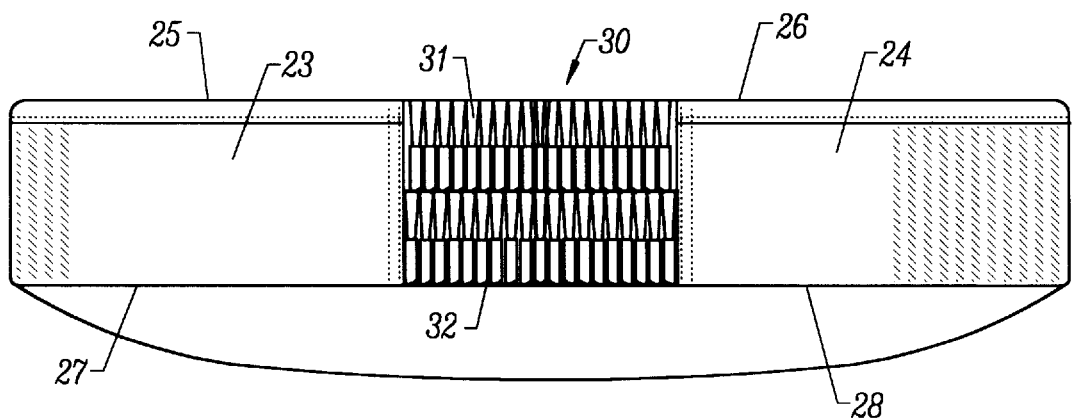
FIG. 3 is an elevational view of the rear of the visor shown in FIGS. 1 and 2.
Figure 4:
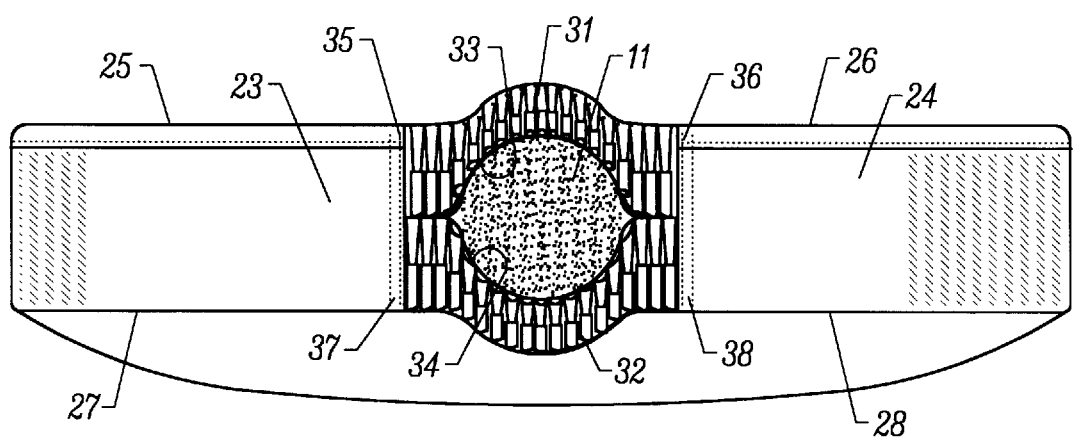
FIG. 4 is a rear elevational view showing schematically how the invention encircles and grasps a ponytail.

A ponytail pull-through means 30 is provided which includes a pair of parallel elastic bands 31 and 32 shown best in FIG. 3. The elastic bands are sewn onto the ends of the fabric band by stitching shown as 35,36,37 and 38 in FIG. 4. Elastic bands 31 and 32 have a first position in which they are slightly extended and parallel with each other, as shown in FIG. 3, in which condition a gentle tensile force is applied holding the headgear to the user's head. The elastic bands 31 and 32 have a second position in which they form a ponytail pull-through, as shown in FIG. 4. The user simply spreads the elastic bands 31 and 32, and pulls ponytail 11 through the opening formed between the bands. The hat or visor is pulled onto the user's head, as shown in FIG. 2. In this second position of the elastic bands 31 and 32, the bands encircle and grasp the ponytail 11 with inner edges 33 and 34, as shown in FIG. 4, and hold the ponytail together. Simultaneously, the bands 31 and 32 in this second position also continue to exert a gentle tensile force holding the headgear onto the user's head.

As shown best in FIG. 3, the preferred design utilizes a uniform height of the fabric band as it extends around the sides of the user's head and across the back portion of the user's head. The top 25 of side portion 23 forms a straight line with the top 26 of side portion 24. Similarly, the bottom 27 of side portion 23 forms a straight line with bottom 28 of side portion 24. The height of the elastic bands 31 and 32 is preferably the same as the height of the fabric band, providing a pleasant appearance of the rear of the device.

The invention provides a simple, but effective, visor or cap with a pleasant appearance. The ponytail pull-through is easy to use and is a single piece design, with no pieces which may separate and get lost during use.

What is claimed is:

1. A headgear apparel device comprising:

a visor;

support means carrying said visor, said support means having a front portion adapted to extend across the front of a user's head and first and second side portions for extending across both sides of a user's head and across a portion of the back of a user's head;

a ponytail pull-through means connected to said first and second side portions of said support means, said ponytail pull-through means including a pair of elastic bands, said elastic bands having a first position in which they extend and stretch parallel to each other to exert a tensile force on said side portions to retain the headgear on a user's head, and a second position in which said elastic bands stretch to form a generally circular shape in which they are adapted to encircle and grasp a ponytail of a user while simultaneously exerting a tensile force on said side portions to retain the headgear on a user's head.

2. The apparatus of claim 1 wherein said support means is fabric.

3. The apparatus of claim 2 wherein said pair of elastic bands is connected to said side portions by being sewn onto said side portions.

4. A head visor adapted to be worn by a user having a ponytail, the head visor comprising:

a visor;

a fabric band carrying said visor, said fabric band adapted to extend around the front, both sides and a portion of the back of a user's head, and having first and second ends;

a pair of elastic bands connected to said first and second ends, said pair of elastic bands having a first position in which they are partially stretched and extend parallel to each other to hold said visor on a user's head, and having a second position in which they are stretched to form a generally circular shape to encircle and grasp a user's ponytail while simultaneously exerting a retaining force to hold the visor on a user's head.

* * * * *